(12) United States Patent
Ahrens et al.

(10) Patent No.: US 8,852,249 B2
(45) Date of Patent: Oct. 7, 2014

(54) BONE PLATE

(75) Inventors: Uwe Ahrens, Berlin (DE); Majid Bakhshi, Berlin (DE); Hans-Joachim Fischer, Berlin (DE)

(73) Assignee: Implantate AG, Berlin (DE)

( * ) Notice: Subject to any disclaimer, the term of this patent is extended or adjusted under 35 U.S.C. 154(b) by 399 days.

(21) Appl. No.: 11/817,651

(22) PCT Filed: Nov. 16, 2006

(86) PCT No.: PCT/EP2006/010985
§ 371 (c)(1),
(2), (4) Date: Nov. 20, 2007

(87) PCT Pub. No.: WO2007/079814
PCT Pub. Date: Jul. 19, 2007

(65) Prior Publication Data
US 2008/0161860 A1    Jul. 3, 2008

(30) Foreign Application Priority Data

Dec. 23, 2005  (EP) .................................... 05028290
May 26, 2006  (EP) .................................... 06010835

(51) Int. Cl.
*A61B 17/80* (2006.01)
*A61B 17/17* (2006.01)
*A61B 17/86* (2006.01)

(52) U.S. Cl.
CPC ......... *A61B 17/1728* (2013.01); *A61B 17/8057* (2013.01); *A61B 17/8605* (2013.01); *A61B 17/8014* (2013.01)
USPC ......................................... 606/291; 606/289

(58) Field of Classification Search
USPC ...................................... 606/70–71, 280–299
See application file for complete search history.

(56) References Cited

U.S. PATENT DOCUMENTS

| 3,552,389 A | 1/1971 | Allgower et al. |
| 3,668,972 A | 6/1972 | Allgower et al. |

(Continued)

FOREIGN PATENT DOCUMENTS

| CA | 2189744 | 9/2003 |
| CH | 462 375 | 9/1968 |

(Continued)

OTHER PUBLICATIONS

Extract from the Register of European Patents for EP1859752, entitled "Bone Plate," found at https://register.epo.org/application?Ing=en&numberEP06010835, dated May 14, 2014.

*Primary Examiner* — Matthew Lawson
(74) *Attorney, Agent, or Firm* — Smith Gambrell & Russell LLP

(57) ABSTRACT

A bone plate comprising a bottom side that is to rest against the bone, an upper side, and a plurality of holes along the longitudinal axis of the plate through which bone screws can be inserted to be anchored to a bone. At least one hole is a continuous oblong hole comprising a longitudinal axis running in the direction of the longitudinal axis of the plate. Thread flights are provided in a partial area of the lateral side of the oblong hole that when in a direction transversal to the plane of the upper side, are arranged only over a part of the depth of the oblong hole. In the direction transversal to the plane of the upper side, a support structure with smooth walls for the positive fit with a correspondingly configured negative structure at a screw head or screw neck of a bone screw is provided.

23 Claims, 14 Drawing Sheets

(56) References Cited

U.S. PATENT DOCUMENTS

| | | | |
|---|---|---|---|
| 3,779,240 A * | 12/1973 | Kondo | 606/282 |
| 4,513,744 A | 4/1985 | Klaue | |
| 5,709,686 A * | 1/1998 | Talos et al. | 606/281 |
| 6,669,701 B2 * | 12/2003 | Steiner et al. | 606/282 |
| 6,719,759 B2 * | 4/2004 | Wagner et al. | 606/282 |
| 7,229,445 B2 * | 6/2007 | Hayeck et al. | 606/70 |
| 7,354,441 B2 * | 4/2008 | Frigg | 606/261 |
| 2002/0120273 A1 * | 8/2002 | Needham et al. | 606/61 |
| 2002/0183752 A1 * | 12/2002 | Steiner et al. | 606/69 |
| 2004/0087951 A1 | 5/2004 | Khalili | |
| 2004/0181228 A1 * | 9/2004 | Wagner et al. | 606/69 |
| 2004/0236332 A1 * | 11/2004 | Frigg | 606/69 |
| 2005/0010226 A1 * | 1/2005 | Grady et al. | 606/69 |
| 2005/0027297 A1 * | 2/2005 | Michelson | 606/71 |
| 2005/0261688 A1 * | 11/2005 | Grady et al. | 606/69 |
| 2006/0004361 A1 * | 1/2006 | Hayeck et al. | 606/69 |
| 2008/0119894 A1 * | 5/2008 | Ehrhardt et al. | 606/280 |
| 2008/0249572 A1 * | 10/2008 | Tandon | 606/280 |

FOREIGN PATENT DOCUMENTS

| | | | | |
|---|---|---|---|---|
| CH | 650 915 A5 | 8/1985 | | |
| DE | 43 43 117 A1 | 6/1995 | | |
| EP | 0 760 632 | 3/1997 | | |
| EP | 1175181 | 1/2005 | | |
| EP | 1 712 197 B1 | 11/2005 | | |
| EP | WO 2006/072379 | * 12/2005 | | A61B 17/58 |
| WO | WO 96/29948 | 10/1996 | | |
| WO | WO 00/53111 | 9/2000 | | |
| WO | WO 00/66012 | 11/2000 | | |
| WO | WO 01/54601 | 8/2001 | | |
| WO | WO 01/54601 A1 | 8/2001 | | |
| WO | WO 2004/084701 | 10/2004 | | |

* cited by examiner

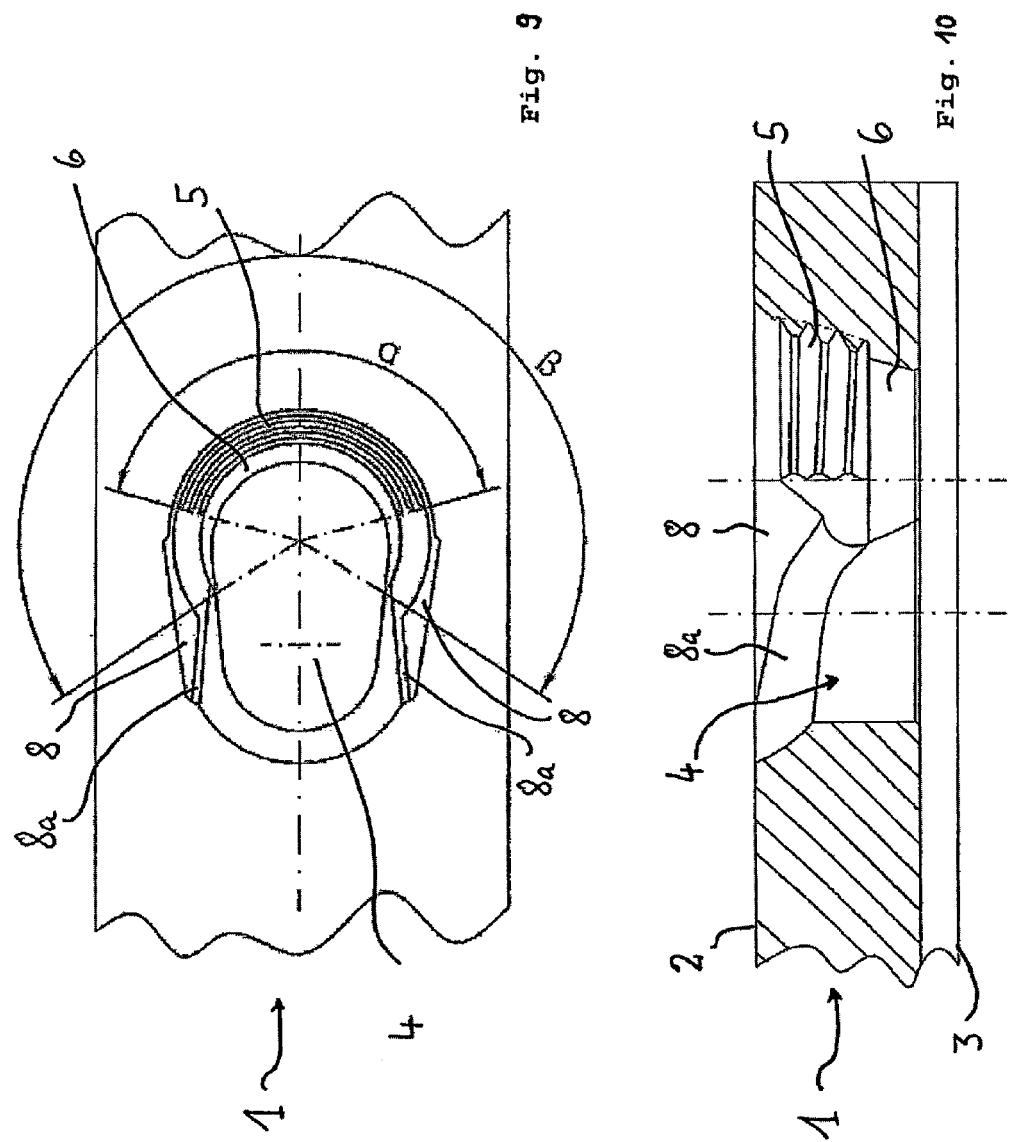

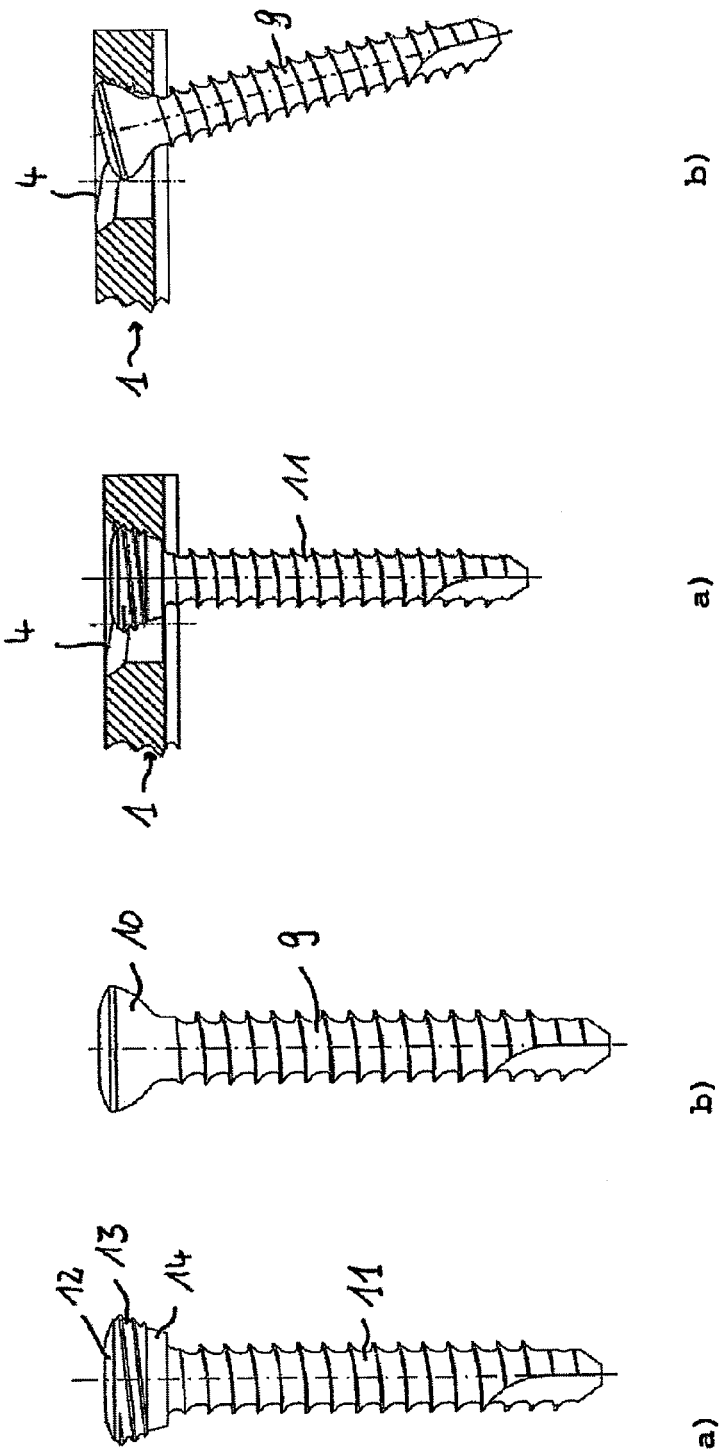

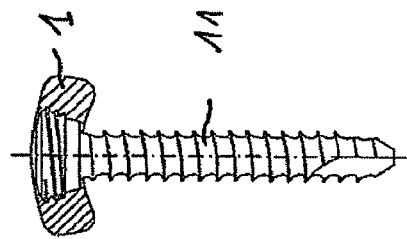
Fig. 15
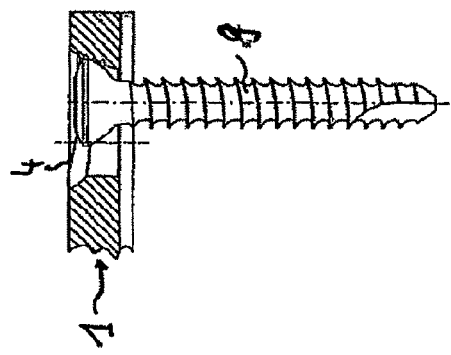
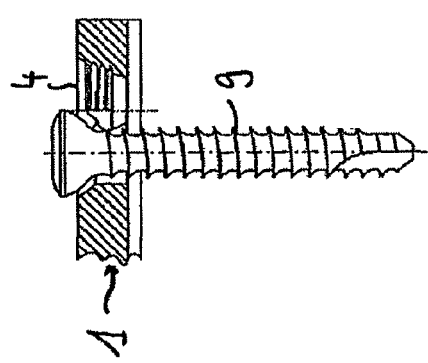
Fig. 14

BONE PLATE

CROSS-REFERENCE TO RELATED APPLICATIONS

This application is a national stage of and claims the benefit of priority of International Patent Application No. PCT/EP2006/010985, filed on Nov. 16, 2006, which claims priority to European Patent Application No. 05028290.4, filed Dec. 23, 2005, and European Patent Application No. 06010835.4, filed May 26, 2006, all of which are relied on and incorporated herein by reference.

BACKGROUND OF THE INVENTION

The invention concerns a bone plate.

Bone plates are known, for example, from CH 462375, WO 2000/53111, WO 2001/54601 or EP 0760632 B1.

The configuration of the holes in this prior art is such that they consist of a combination of two intersecting holes with different diameters and are combined into a continuous hole, and each side of the continuous hole with its fixed diameter has its own functionality and also needs to be considered separate from each other.

Thus, for example, it is not possible to use a standard cortical screw at the thread side of the continuous hole, but instead only a screw with headed thread.

The other side of the continuous hole, not having a threaded part, is only suitable for insertion of a standard cortical screw, which can also be applied with compression and angle variability.

Thus, one could also separate the holes entirely from each other, since they have no functional interfaces.

This drawback then runs as well throughout the entire application, for when inserting a standard cortical screw one must also make sure that it is located on the proper side of the continuous hole.

From U.S. 2004/0087951 there is known a bone screw having a threaded segment and smooth-wall segments arranged one on top of the other on its screw head, looking in the direction of the longitudinal axis of the screw. These smooth-wall segments serve for a flexible receiving of the screw in corresponding guideways.

BRIEF SUMMARY OF THE INVENTION

Based on the above, the problem of the invention is to improve the usage possibilities of a bone plate and enhance its flexibility of manipulation.

This problem is solved by one embodiment of a bone plate comprising a bottom side that is to rest against the bone and an upper side opposite to the bone as well as a plurality of holes located preferably along the longitudinal axis of the plate, through which bone screws can be inserted to be anchored to a bone, wherein at least one of these holes is a continuous oblong hole comprising a longitudinal axis running in the direction of the longitudinal axis of the plate, wherein thread flights are provided in a partial area of the lateral side of the oblong hole, said thread flights, when seen in a direction transversal to the plane of the upper side, are arranged only over a part of the depth of the oblong hole, characterized in that, in the direction transversal to the plane of the upper side, above and/or below the thread flights, a support structure with smooth walls for the positive fit with a correspondingly configured negative structure at a screw head or screw neck of a bone screw is provided. Advantageous modifications are indicated in further embodiments. Finally, in another embodiment, a system is indicated, comprising of a bone plate according to the invention and at least one bone screw suitable for it, which can be regarded as a fixation system on the whole.

The essence of the invention for the new bone plate is that both a thread and a smooth-wall support structure are arranged in a partial segment, uniformly one on top of the other, looking in a direction transverse to the plane of its upper side. Thanks to the interplay of thread and smooth-wall support structure, a bone screw with correspondingly configured negative structures can be held in the bone plate especially effectively, locked in position and protected against tilting. Thanks to the interplay of the thread in the oblong hole with a correspondingly fashioned counterthread on the head or neck of the bone screw, the bone screw is pressed firmly into the support structure with a negative structure or bearing structure corresponding in shape to the support structure and thus fixed securely.

In one preferred embodiment, the thread flights in the bone plate of the invention extend along a shorter segment of the oblong hole than the smooth-wall support structure. This technical measure allows in practical use an easy and secure sliding of a bone screw provided with a thread at its neck and/or head and with the negative structure into the structures (thread, support structure) arranged at the oblong hole with a continuous movement of the bone screw along the oblong hole. A sliding transition to a smooth-wall support structure is easier to realize than a sideways sliding into a thread. Thus, the guiding for a secure and accurate transition of the thread at the head and/or neck of the bone screw can be accomplished by the initially occurring interaction between support structure and negative structure, dictating the direction.

Preferred angle ranges for the wrap of the thread arranged on the head and/or neck of the bone screw and engaging with the thread of the oblong hole are $60°\leq\alpha\leq190°$, preferably $60°\leq\alpha\leq180°$, and for the corresponding wrap of the negative structure, $185°\leq\beta\leq300°$. These values were best suited in tests for a preferably continuous movement of the screw along the oblong hole, while still ensuring firm support for a bone screw secured in the thread/support structure of the oblong hole. A free mobility of a bone screw along the longitudinal axis of the oblong hole makes it possible to use this both to apply a pressing force directed onto the point of fracture and to lock the plate angle-fixed.

Especially in a preferred modification the thread looking in the plane of the upper surface engages at most 180 degrees of a circular circumference of a screw head or neck of a bone screw, to be brought into engagement with the latter. This configuration has the effect that a bone screw can move freely along the longitudinal axis of the oblong hole, and thus it can be used both to apply a pressing force directed onto the point of fracture and to lock the plate angle-fixed.

At present, a conical surface is preferred as the support structure. In such a structure, a correspondingly conically shaped surface (negative structure) of the head or neck of the bone screw can be secured. In theory, it is also possible to use other shapes for the surfaces of the support structures, for example, hemispherical surfaces.

It basically makes no difference to the bone plate of the invention whether the supporting structure is arranged first, seen from the upper side of the plate, and the thread is arranged in the lower region of the bone plate, or vice versa. One just as well have several thread segments in the bone plate, each of them alternating with and interrupted by at least one segment with a support structure. Preferred is a sample embodiment in which the threaded segment lies near the upper side of the bone plate and a support structure lies near the lower side of the bone plate.

A recess in the transitional region between thread and support structure facilitates the passage of the screw head or neck, more precisely, the region provided with the thread, into the segment of the oblong hole provided with the thread, especially when pushing the bone screw along the oblong hole.

In one embodiment, the oblong hole has a first guide structure at the upper side of the bone plate. This serves to guide the head or neck of a bone screw. This guide structure can be, for example, a circumferential margin with cross section in the form of a semicircle, in which a correspondingly spherical or hemispherical negative structure on the head or neck of a bone screw can slide. The guide structure defines a guideway. This guideway is a path, lying preferably in a plane, along which an imaginary point on the screw head slides when the screw is shoved along the guide structure. Moreover, this guideway is intersected by a longitudinal axis of the thread, which in the sense of the invention is the axis about which a counterthread rotates when being screwed into the thread, at an angle different from 90 degrees. This kind of tilting between thread and guide plane has the effect that, even for a maximum wrap of 180 degrees situated in the plane of the surface, the thread or the support structure provides a rather firm support to the screw head or neck, since the tilting leads to an effectively greater wrap, at least in a partial region of the thread. This effect is achieved by a "clamping" or "wedging" effect, produced by the tilting.

Furthermore, it is preferable that the guideway be inclined by an angle between 0 and 90 degrees relative to the plane of the plate. Here, moreover, an embodiment is preferred in which the thread and the support structure are arranged in a segment of the oblong hole in which the guide plane lies deepest, i.e., furthest away from the upper side of the bone plate.

The segment of the oblong hole provided with thread and support structure, according to the invention, is limited to a partial segment of the oblong hole, which lies preferably on a narrow side of the oblong hole.

Advantageously, the oblong hole of the invented bone plate has a second guide structure, besides the first guide structure described above, serving to guide bone screws with threadless head and neck (standard cortical screws). This separation of the guide structures allows for a more clean separation in the action of the two bone screws which can possibly be employed with the invented bone plate.

By oblong hole in the sense of this invention is meant not only a hole pattern produced by displacing a circle along a linear axis, but basically any shape of an opening which is longer in a first dimensional direction than in a second dimensional direction. Thus, an oblong hole in the sense of the invention can also have a "triangularly tapering", oval, or "keyhole-shaped" configuration. Preferably, this oblong hole is continuous, i.e., with no "barriers" protruding into the hole.

Finally, the invention specifies a system comprising of a bone plate as described above and a bone screw. The bone screw of this system has, according to the invention, a screw head or screw neck, on which it has a thread structure and a bearing structure configured complementary to the support structure of the oblong hole, being arranged one on top of the other and matching up with the corresponding negative structures in the bone plate.

The bone plate can be stable-angle fixed and tightened at the same time with a bone screw, configured specially with a thread and a negative structure on the screw head and/or neck. However, it should be emphasized here that the bone plate of the invention can also be fixed with standard bone screws or bone screws derived from such standard bone screws, in particular, ones having neither a thread nor a negative structure at their screw head or neck.

The bone plate of the invention—also together with the invented bone screw—offers a great variety of possible applications, which makes it suited for the fixation of the most diverse fractures.

For this, it is especially preferred that all openings in the bone plate be configured as oblong holes with the properties of the invention.

BRIEF DESCRIPTION OF THE DRAWINGS

Additional benefits and features of the invention will emerge from the following description of a sample embodiment by means of the enclosed drawings. These show.

The figures show schematically sample embodiments of a bone plate according to the invention and all of them are generally designated with 1. The sample embodiments shown are in no way true to scale, but serve merely as a basic illustration.

DETAILED DESCRIPTION OF THE INVENTION

Figure 1:
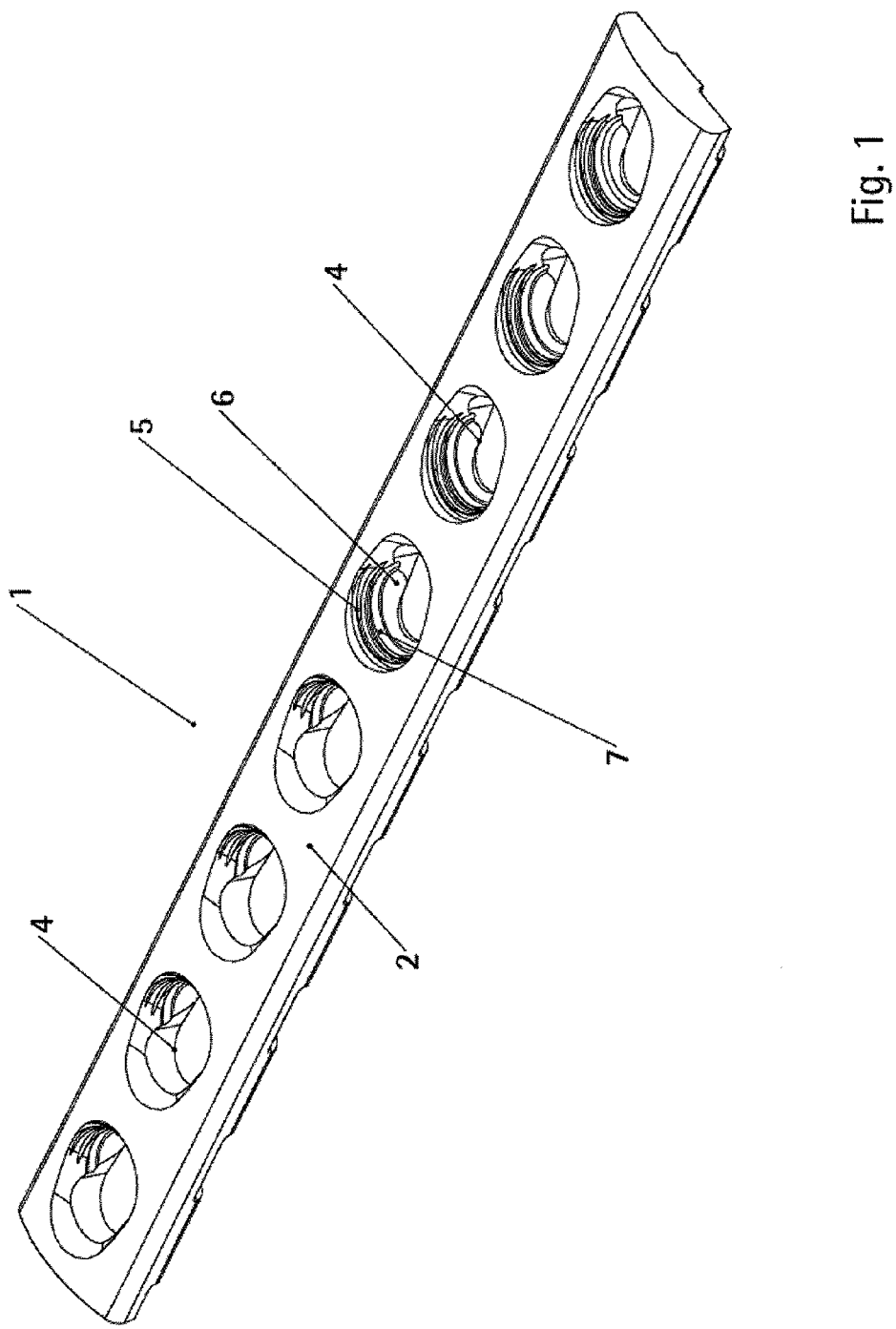
FIG. 1, a first sample embodiment of the invented bone plate in a three-dimensional view, FIG. 2, the bone plate of FIG. 1 in a view from above, FIG. 3, the bottom side of the bone plate from FIG. 1, in an enlarged cutout, FIG. 4, the bottom side of an alternative embodiment of the invented bone plate, in an enlarged view, FIG. 5, a cross section through a bone plate from FIG. 1 along its central longitudinal plane, FIG. 6, a cross section according to FIG. 5, in enlarged view, with only one oblong hole depicted, FIG. 7, a view as in FIG. 6 with the course of the guide structure drawn for clarity, FIG. 8, a sample embodiment of a bone plate according to the invention, in a top view, FIG. 9, in an enlarged cutout, the top view of an oblong hole of a sample embodiment of the invented bone plate, FIG. 10, in an enlarged view, a longitudinal section through the oblong hole of FIG. 2, FIG. 11 a) a front view of a bone screw with thread and negative structure formed on its screw head to interact with the thread and the support structure in the invented bone plate, and b) a front view of a standard bone screw, FIG. 12 a) a front view, comparable to FIG. 4 a), of a bone screw for interworking with the thread and the support structure in the invented bone plate and b) a front view of a standard bone screw in one possible position in the oblong hole for fixation of the bone plate, FIG. 13, sequence consisting of three individual views to illustrate the sliding of the bone screw, provided with thread and negative structure on its screw head, into the segment of the oblong hole with thread and support structure, FIG. 14, a sequence in two individual views, similar to FIG. 6, to illustrate the sliding of a standard bone screw into the segment of the oblong hole with thread and support structure, FIG. 15, the firm seating of a bone screw provided with thread and negative structure in the thread and the support structure of the oblong hole in a section view transverse to the lengthwise dimension of the bone plate, FIG. 16 a) to c) three different possible additional shapes of an oblong hole of an invented bone plate.
Figure 2:
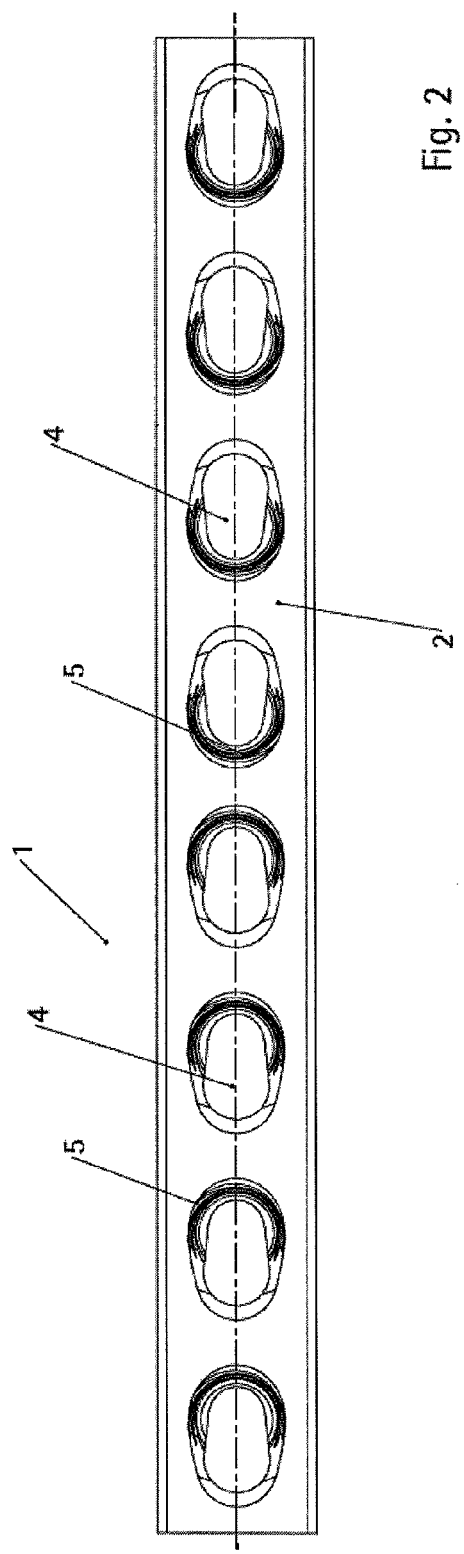
Figure 3:
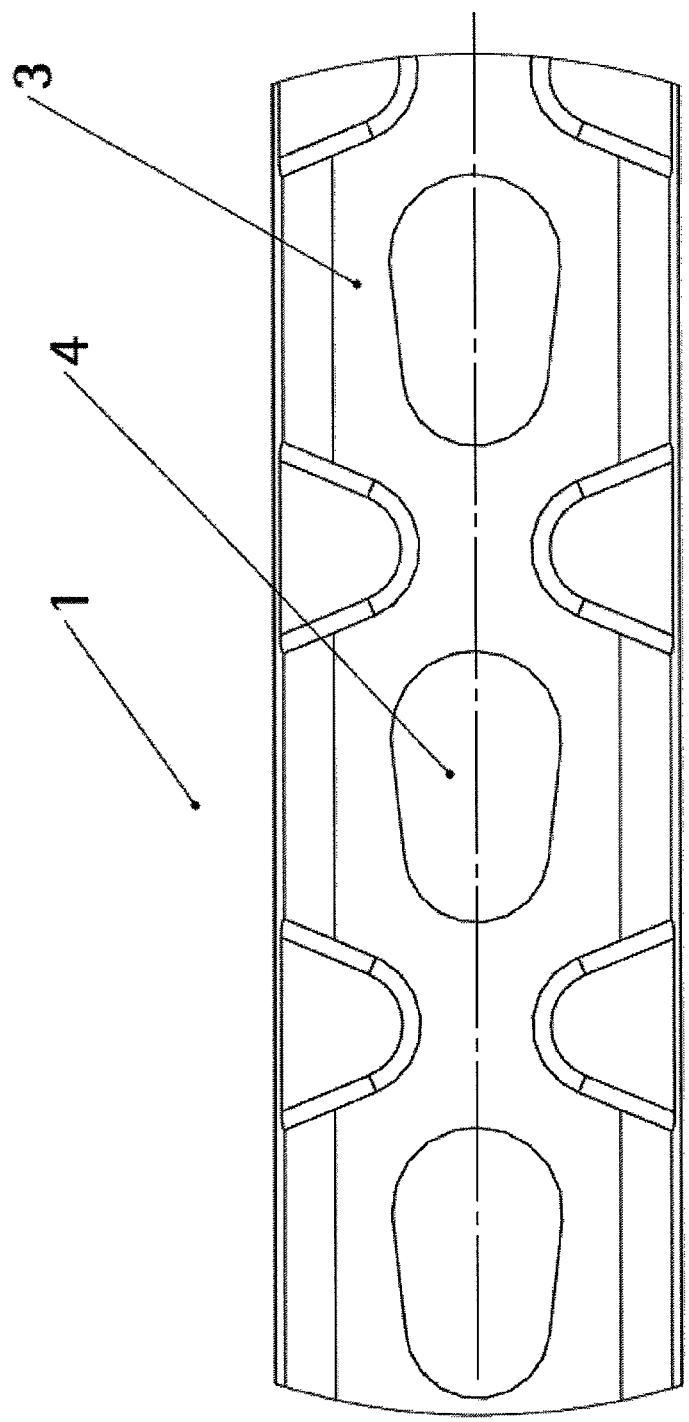
Figure 4:
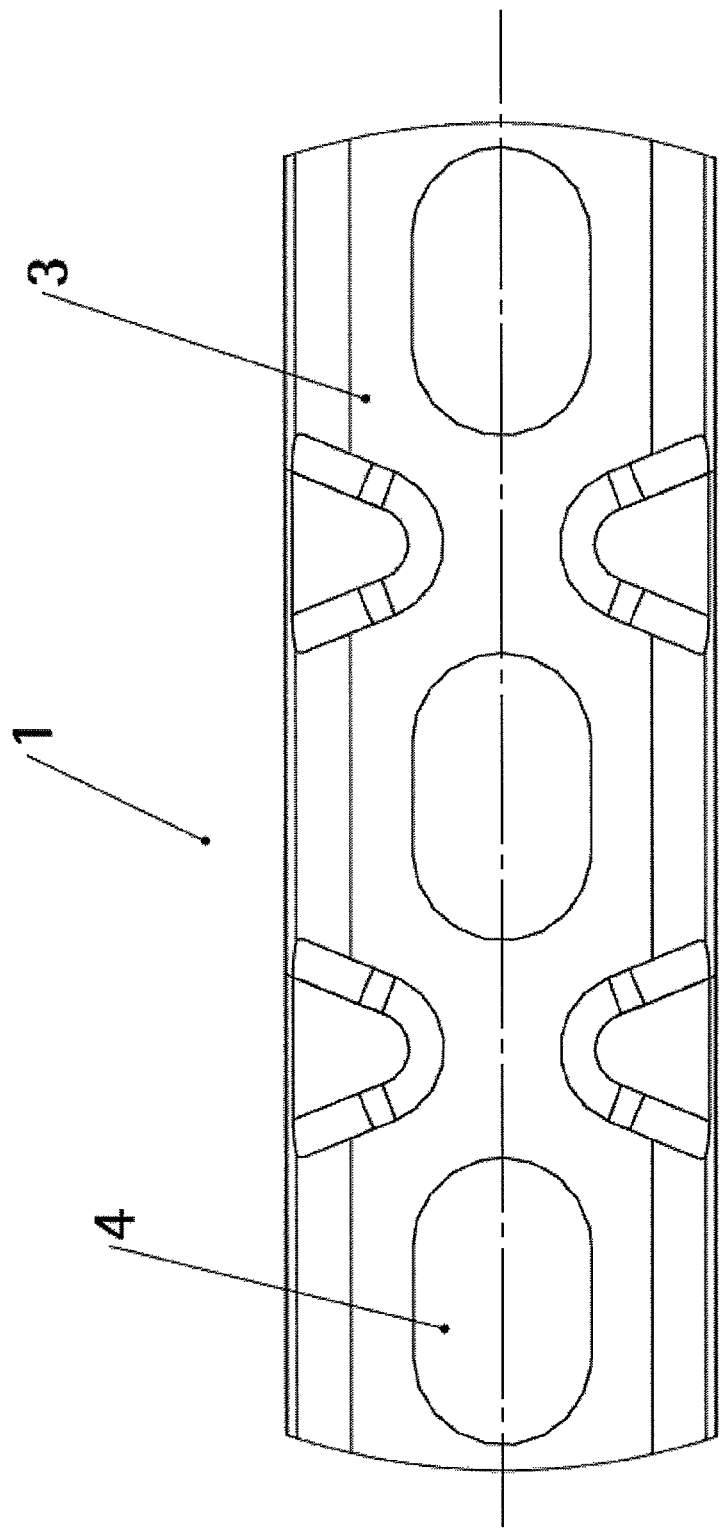
Figure 5:
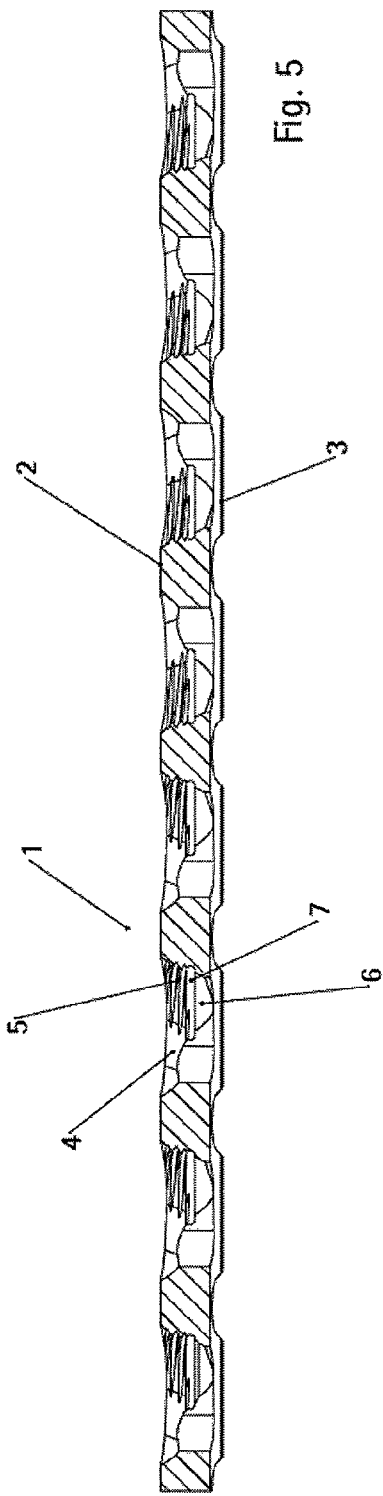
Figure 16:
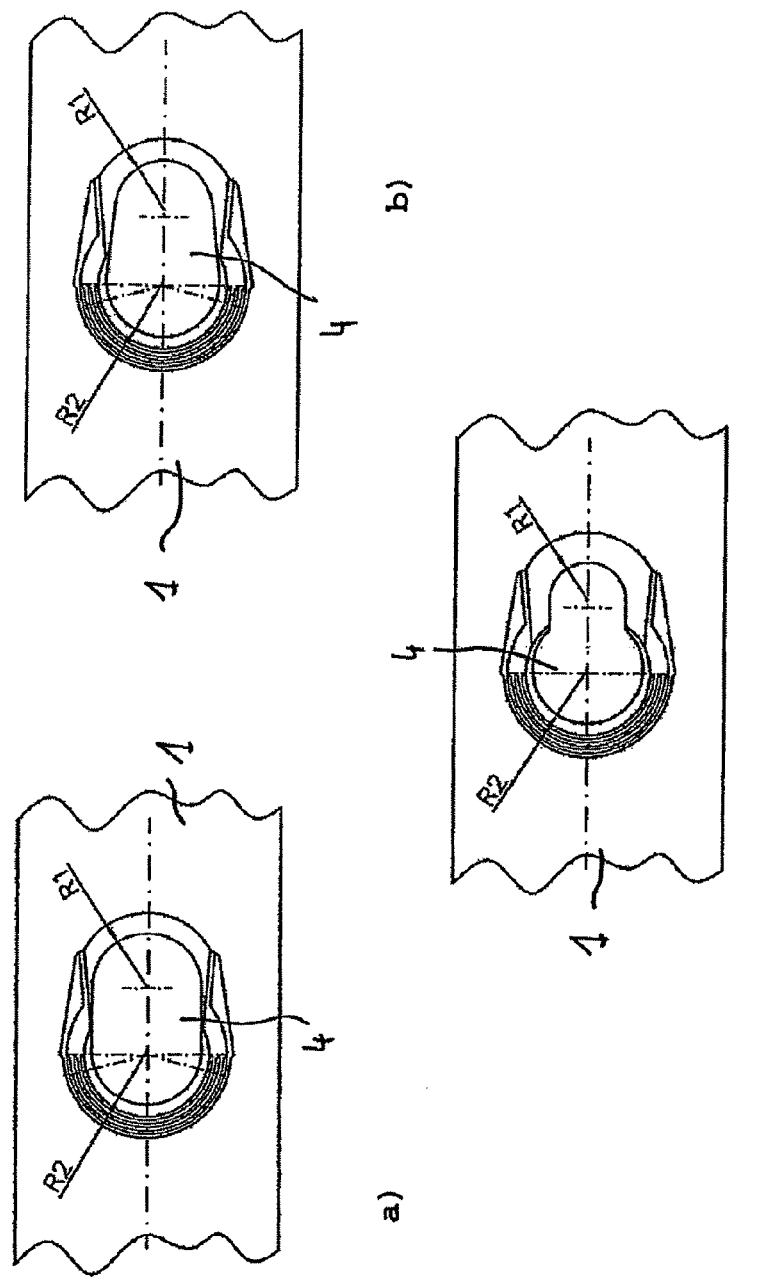

The invented bone plate 1 has an upper side and a lower side 3, serving to bear against the bone being fixated. Continuous openings in the form of oblong holes 4 are introduced into the bone plate between upper side and lower side. The oblong holes 4 are continuous in these sample embodiments, i.e., configured without any projections or similar obstructions reaching into the interior. The invented bone plate 1 has eight oblong holes 4 overall in these sample embodiments, yet without being limited to this number. The oblong holes 4 are configured as narrowing toward one of the lengthwise sides in the preferred sample embodiments. However, as is shown for example in an alternative embodiment per FIG. 4, they can also have a straight course and correspond to the shape produced by displacing a circle along a predetermined distance. Of course, all other conceivable shapes of oblong holes are also possible, as long as they are continuous in form, i.e., free of obstruction in their interior. Corresponding examples are presented in FIGS. 16 a) to c).

Figure 6:
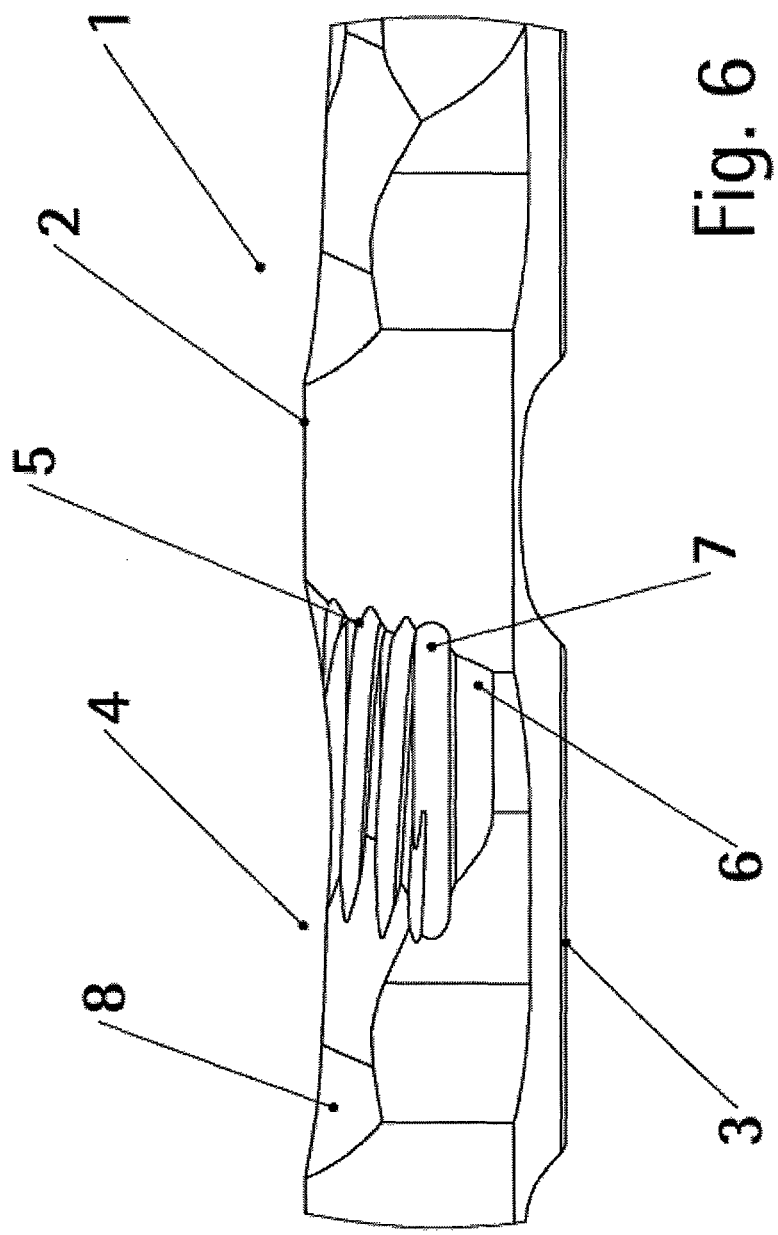

At one end face of each oblong hole are formed a thread or thread flights 5, as well as a support structure 6. The thread 5 and the support structure 6 lie one above the other in a direction transversely to the plane of the plate, while in these sample embodiments the thread 5 is arrange on top (toward the upper side 2 of the bone plate 1) and the support structure 6 underneath (toward the lower side 3 of the bone plate 1). In the transitional region between thread 5 and support structure 6, a recess 7 can be introduced (see FIG. 6). However, this recess is not absolutely essential, and it is not present in the variant embodiments shown in FIGS. 8 through 13, for example. The support structure 6 is formed by a smooth-walled segment of the oblong hole, being hemispherical in the sample embodiment shown in FIGS. 1 to 7, or conical in the sample embodiment shown in FIGS. 8 to 13.

As is especially evident in FIGS. 1, 2, 3, 8, 9 and 16, the thread 5 and support structures 6 of the oblong holes 4 in the sample embodiments shown there are arranged at the narrow sides of the latter, usually at the tapered narrow sides, being oriented in the direction of the middle of the plate. The longer lengthwise axes of the oblong holes 4 run along a lengthwise axis of the plate.

Figure 7:
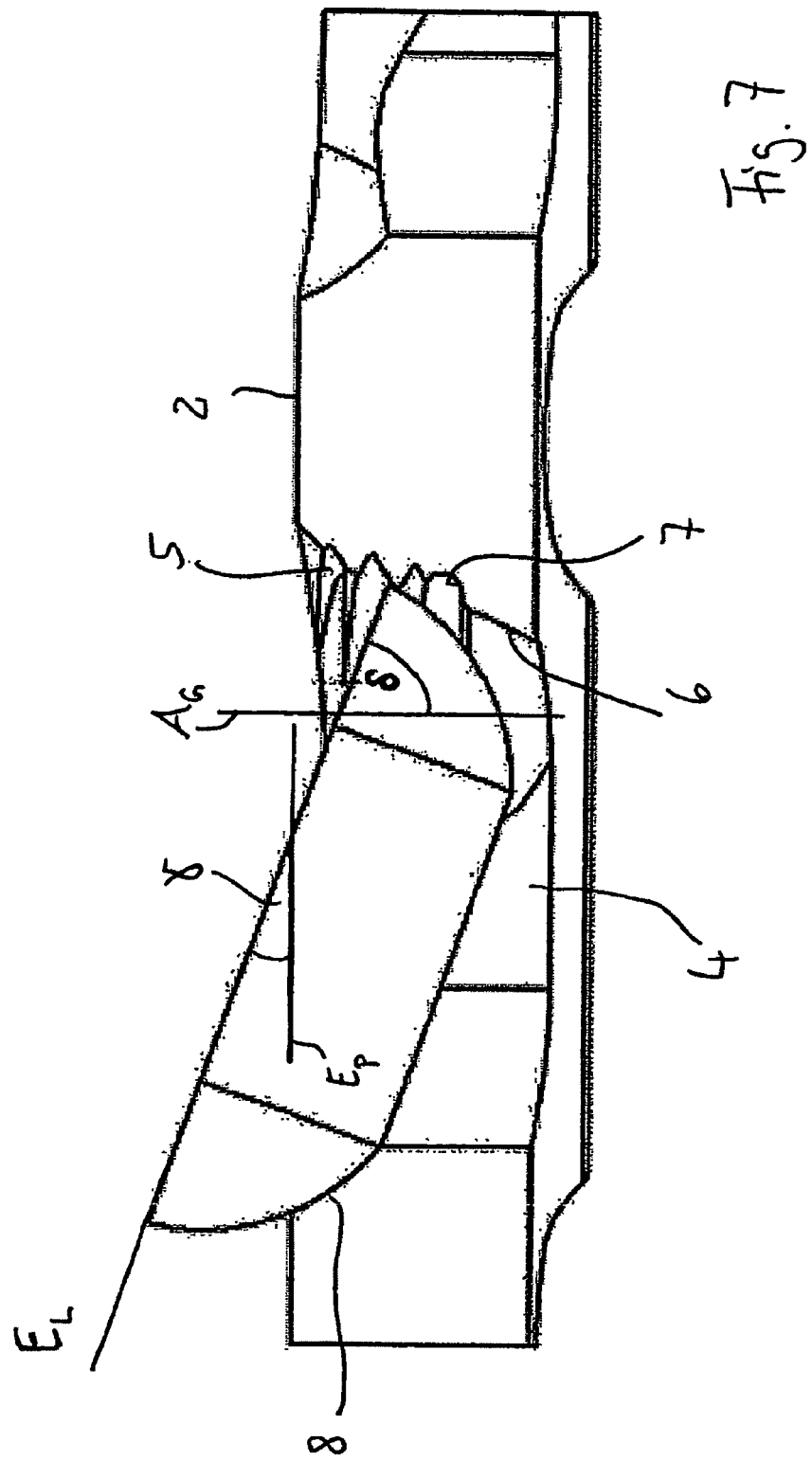

The oblong hole 4 contains a circumferential guide structure 8 at its opening facing the upper side 2 of the bone plate 1. This is formed by a margin with semicircular cross section, which is introduced in the oblong hole 4, for example, by a chip-removal machining step (such as milling). As an illustration of this, FIG. 7 shows a "bathtub" shaped trend of this margin, i.e., the guide structure 8. One also notices here that the guide structure 8 is inclined at an angle γ to the course of the plane of the plate $E_P$, dictated by the trend of the upper side 2 of the bone plate 1. Likewise, the guideway or guide plane $E_L$ is also inclined relative to a lengthwise axis $A_G$ of the thread, and this by an angle 6.

Figure 8:
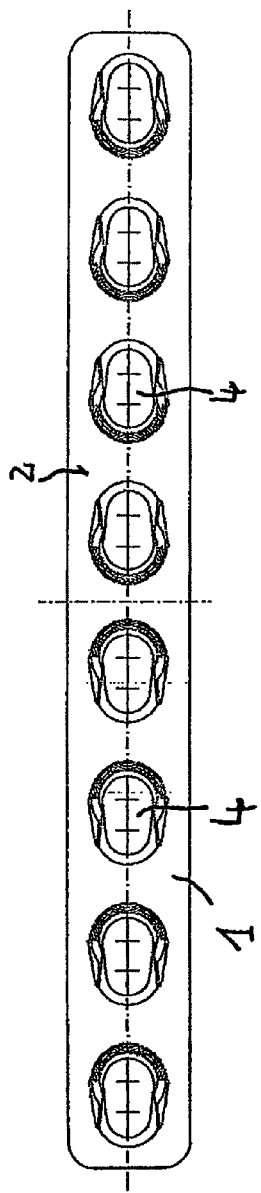
Figure 13:
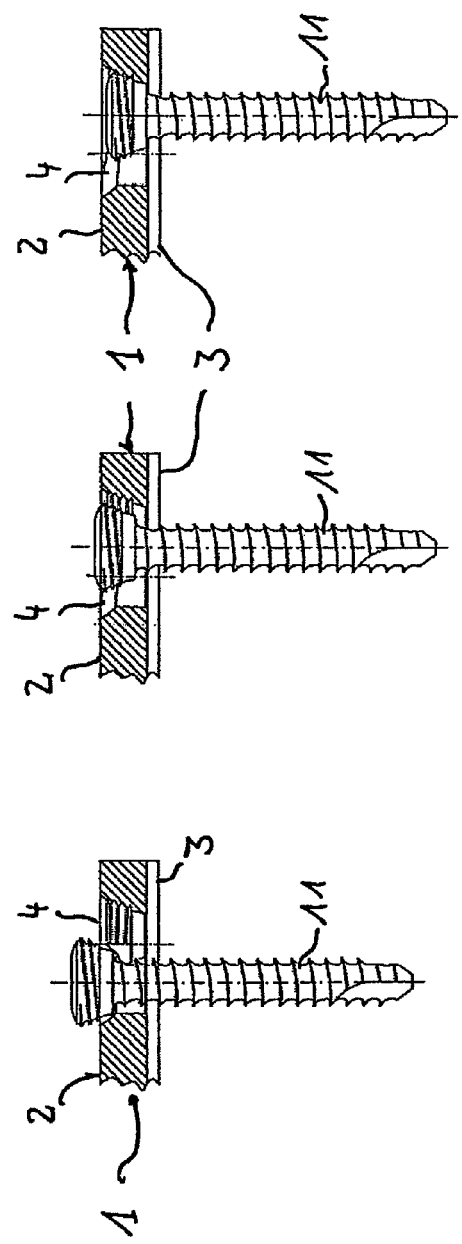

In particular, it is evident from FIG. 9 that the thread flights 5 in the sample embodiments shown in FIG. 8 to 10 and also 16 run in a shorter circumferential segment of the oblong hole 4 than the support structure 6. While the former extend over an angle α of preferably between 60 and 190 degrees, the latter extends over an angle range β of preferably between 185 and 300 degrees. This choice of different wrap regions allows for a smooth sliding of the bone screw into this region with a reliable fixation at the end, as shall be further explained below.

FIGS. 11a) and 11b) show a bone screw 11 with a screw head 12 specially designed for interworking with the invented bone plate 1 and a standard bone screw 9 with a screw head 10 shaped smooth and spherical at the bottom side. The screw head 12 contains at an upper segment a thread 13 which is spherically configured in this sample embodiment and, underneath this, looking in the direction of the lengthwise axis of the screw, a segment with a bearing or negative structure 14. This bearing structure 14 is smooth walled in this sample embodiment with partly spherical or conical trend, tapering in the direction of the screw tip and matched to the support structure 6 of the particular sample embodiment, and it is complementary to the shape of the support structure 6 of the bone plate 1.

The oblong hole 4 in the sample embodiment shown in FIG. 8 to 10 contains two guide structures 8 and 8a at its opening facing the upper side 2 of the bone plate 1. While the first guide structure 8 is a guide structure for the guiding of a bone screw 11 with thread 13 and bearing structure 14 at the screw head 12, the guide structure 8a serves to guide the screw head 10 of a standard bone screw 9. The two guide structures 8, 8a are arranged one on top of the other, formed by a margin with semicircular cross section, which is made in the oblong hole 4, for example, by a chip-removal machining step (such as milling). The two guide structures 8, 8a each define a guideway, running at an inclination to the surface of the bone plate 1. In particular, the first guide structure 8 (or the guideway defined by it), as in the previously described sample embodiment, intersects the plane of the plate, determined by the trend of the upper side 2 of the bone plate 1, at a first angle other than 0 and 90 degrees. Likewise, the guideway is also inclined relative to a lengthwise axis of the thread, and this likewise at an angle other than 0 and 90 degrees.

FIGS. 12a) to 14 show the interworking between a bone screw 9 of the traditional kind and a bone screw 11 of the adapted kind in the invention and the bone plate 1 of the invention. Thus, the functioning of the bone plate 1 of the invention and its elements shall now also be explained by means of these figures.

FIGS. 12b) and 14 show a traditional bone screw 9 inserted into the oblong hole 4 of the bone plate 1, in two different positions. This bone screw 9 lies with the smooth, spherically formed underside of the screw head 10 against the complementary formed guide structure 8 (in the first sample embodiment) or 8a (in the second sample embodiment) of the oblong hole 4 and can thus be shoved along the lengthwise axis of the oblong hole 4, following the guideway dictated by this guide structure. Due to the slanted position of the guideway, a compression effect is achieved when screwing in the bone screw 9, such that the bone plate 1 is pressed in a direction or a bone being fixed therewith is pulled in the other direction. In particular, the outer contour of the thread segment formed by the thread flights 5 in the oblong hole 4 is formed such that it also forms a guide surface shaped complementary to the conically shaped underside of the screw head 10. This outer contour thus forms part of the guide structure 8 and 8a. At this guide surface, the traditional bone screw 9 can become tilted relative to the vertical (corresponding to the direction of the thread axis). This gives a multitude of possibilities for securing the bone screw 9 in the bone. This tilting is possible not only in a direction along the lengthwise axis of the oblong hole, but also in directions transverse to it, so that ultimately one has a region of basically 360 degrees in which the screw can be tilted relative to the thread axis.

Such a traditional bone screw 9 can be used with the bone plate 1 of the invention to achieve a compression effect. However, this bone screw is not suitable to achieving an angle-stable securing in bone plate 1 and bone. For this, one can use the bone screw 11 adapted to the bone plate according to the invention, as shall now be described with the help of FIGS. 12a) and 13 to 14.

The segment of the screw head 12 provided with the thread 13 has an outer contour (an envelope of the thread flights), which is likewise spherical and complementary to the contour of the guide structure 8. In this way, the bone screw 11 can be led into the guide structure 8. Thus, the bone screw 11 can also be used initially to accomplish a compression effect. But the peculiarity of the bone screw 11 is that it can be secured in stable position in the oblong hole 4 of the bone plate 1. This situation is shown, e.g., in FIG. 5a). In this position, the thread 13 of the screw head 12 engages with the thread flights 5 in the oblong hole 4, and the bearing structure (negative structure) 14 lies with positive fit against the support structure 6. Thanks to the interworking of the thread flights 5 with the thread 13, the bearing structure 14 is pressed firmly against the support structure 6, while it should be noted that the support structure 6 and the thread flights 5 are coaxially configured, just like the thread 13 and the bearing structure 14 on the screw head 12. The transition from the screw head 12, more precisely, the thread 13 on the screw head 12, to the thread flights 5 in the oblong hole 4 is facilitated and guided by the initially occurring contact between the negative structure 14 and the support structure 6, which contact dictates a definitely guided movement. Thus, the start of the thread flight of the thread 13 can be taken securely into the thread flights 5, so that the thread 13 ultimately engages with the thread flights 5, without tilting.

In a position as shown by FIG. 12a), the thread flights 5 enclose the screw head 12 and the thread 13, looking in a plane of the surface 2 of the bone plate 1, preferably by not more than 180 degrees. The screw 11 is held in its position by a clamping effect, achieved by the tilting of the guideway dictated by the guide structure 8 relative to the lengthwise axis of the thread, and by the interworking of the support structure 6 (continuing to enclose it in the second sample embodiment of the bone plate 1) with the negative structure 14, while the negative structure 14 is pressed axially into the support structure 6 by the interworking of thread flights 5 and thread 13.

Only thanks to this fact is it possible to configure the oblong hole 4 as continuous and serviceably over its full length for either compression or for angle-stable fixation.

Figure 17:
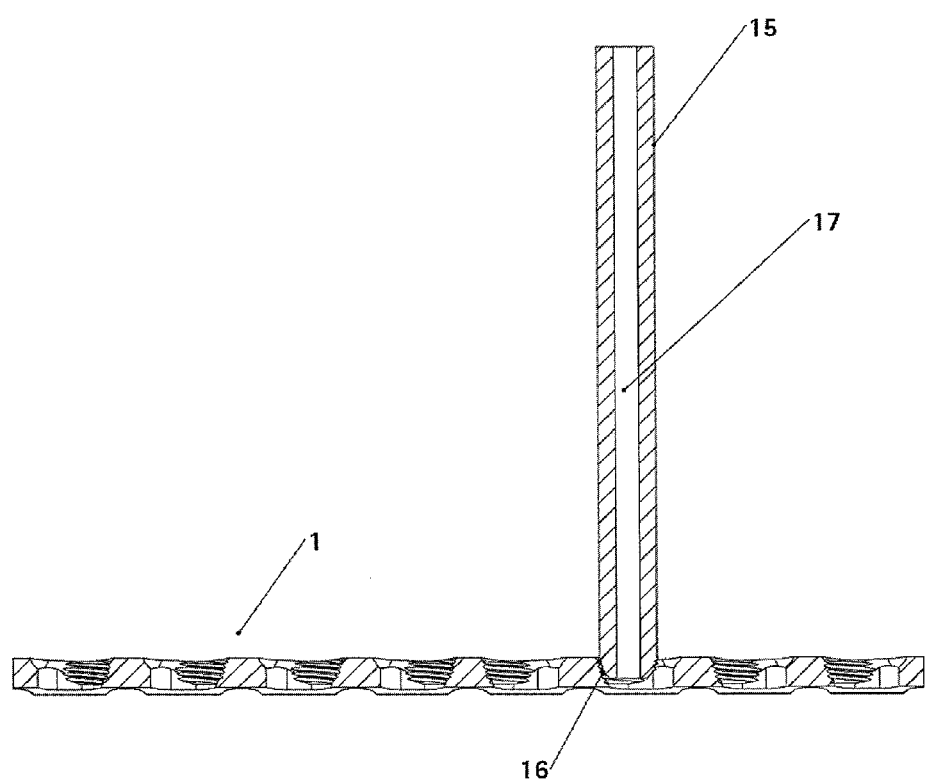
FIG. 17, a front view of the invented bone plate with drill jig sleeve mounted to drill a screw hole in a bone, and FIG. 18, a front view similar to FIG. 14, but with an alternative variant of a drill jig sleeve.
Figure 18:
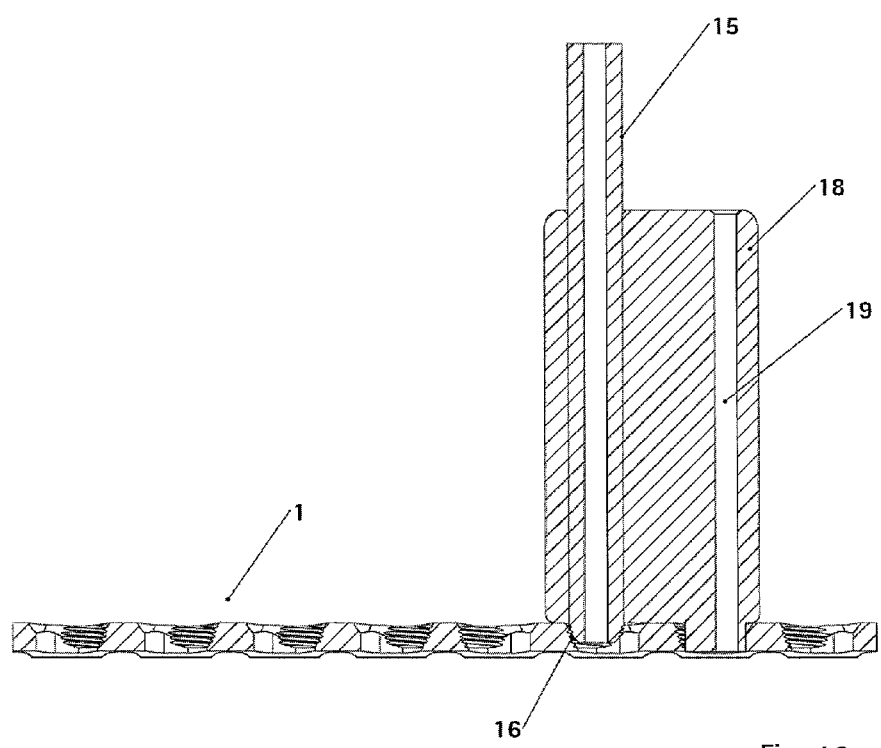

FIGS. 17 and 18 show how the sleeves of drill jigs are connected to the bone plate for the operation to install the bone plate. The situation shown in FIG. 17 shows a simple drill sleeve 15, which is screwed by a spherical thread 16 and bearing structure formed at its lower end (corresponding to the structures on the screw head 12 of the bone screw 11) into the thread 5 and the support structure 6 on the inside of the oblong hole 4. The drill sleeve 15 affords a drilling channel 17 on its inside, which thanks to the proper fitting of the thread 16 and the bearing structure of the drilling sleeve 15 runs along the axis $A_G$. The drilling sleeve 15 serves as an aid when drilling a hole in the bone being provided with the bone plate 1 to make sure that the drilled hole is perpendicular to the bone plate 1 and therefore a bone screw 11 can be screwed into the bone with stable angle, so that its screw head 12 with the thread 13 and the bearing structure 14 easily engages in the thread 5 and the support structure 15.

FIG. 18 shows a variant, in which an additional drilling sleeve 18 is placed onto a drilling sleeve 18 so that the drilling channel 19 of this drilling sleeve 18 lies exactly parallel to the axis $A_G$. With this drilling sleeve 18, one can drill screw holes in the bone, permitting the above-described dual function of a bone screw 11. The bone screw 11 is screwed into the bone at such a perpendicular angle as allows it to slide initially along the inclined plane $E_L$ of the guide structure 8 for a compression and then to engage by the thread 13 and the bearing structure 14 on its screw head 12 securely and without tilting in the thread 5 and the support structure 6 on the inside of the oblong hole 4, so as to become fixed in its angle at the end of the process. Thus, this enables a simultaneous compression and angle fixation in a single step with only a single screw.

The drilling sleeves shown are purely for example, and there are various ways of achieving the same results with drilling sleeves of different design.

Although the invention herein has been described with reference to particular embodiments, it is to be understood that these embodiments are merely illustrative of the principals and applications of the present invention. Accordingly, while the invention has been described with reference to the structures and processes disclosed, it is not confined to the details set forth, but is intended to cover such modifications or changes as may fall within the scope of the following claims.

LIST OF REFERENCE NUMBERS 1 bone plate
2 upper side
3 lower side
4 oblong hole
5 thread/thread flights
6 support structure
7 recess
8 guide structure
8a guide structure
9 bone screw
10 screw head
11 bone screw
12 screw head
13 thread
14 negative structure/bearing structure
15 drill jig sleeve
16 thread
17 drill channel
18 drill jig sleeve
19 drill channel
$A_G$ lengthwise axis of thread
$E_L$ guide plane/guideway
$E_P$ plane of the plate
α angle
β angle
δ angle

The invention claimed is:
1. A bone plate comprising:
a bottom side for resting against a bone;
an upper side opposite the bottom side in a plane; and
a plurality of holes located along a longitudinal axis of the plate for inserting one or more bone screws to be anchored to a bone, wherein at least one hole is a continuous oblong hole having two arcuate segments at opposite ends and two parallel linear portions connecting the arcuate segments with no barriers protruding into the hole, said oblong hole including
a longitudinal axis between said two arcuate segments running in the direction of the longitudinal axis of the plate,
thread flights provided in a partial area of a lateral side of the oblong hole, wherein said thread flights, when seen in a direction substantially transverse to the plane of the upper side, are arranged only over a part of the depth of the oblong hole; and a support structure with smooth walls configured for a positive fit with a correspondingly configured negative structure at a screw head or screw neck of a bone screw is provided above or below the thread flights in the direction substantially transverse to the plane of the upper side.

2. A bone plate according to claim 1, wherein the thread flights extend along a shorter contour segment of the oblong hole than the smooth-wall support structure.

3. A bone plate according to claim 2, wherein the smooth-walled support structure looking in the plane of the surface is configured to enclose an angular region (β) of a circular contour of a screw head or neck of a bone screw to be brought into engagement with the support structure, and wherein $185° \leq \beta \leq 300°$.

4. Bone plate according to claim 1, wherein the thread flights looking in the plane of the surface are configured to enclose an angular region α of a circular contour of a screw head or neck of a bone screw, to be brought into engagement with this, and wherein $60° \leq \alpha \leq 190°$.

5. A bone plate according to claim 1, wherein the support structure is a conical surface.

6. A bone plate according to claim 1, wherein the support structure is a hemispherical surface.

7. A bone plate according to claim 1, wherein the thread flights are arranged in a segment located near the upper side of the bone plate, the support structure in a segment arranged near the lower side.

8. A bone plate according to claim 1, wherein a recess is provided in a transitional region between thread flights and support structure.

9. A bone plate according to claim 1, wherein the oblong hole has, on the upper side of the bone plate, a first guide structure for guiding the head or neck of a bone screw provided with thread flights and a negative structure on its head or neck, and wherein the first guide structure defines a guideway ($E_L$) that is intersected by a longitudinal axis ($A_G$) of the thread formed by the thread flights, at an angle (δ) other than 90 degrees.

10. A bone plate according to claim 9, wherein the guideway ($E_L$) is inclined relative to the plane of the plate (Eρ) by an angle (γ) larger than 0 and smaller than 90 degrees.

11. A bone plate according to claim 10, wherein the thread flights are arranged on a narrow side of the oblong hole, preferably symmetrically to its longer axis, and in this region of the oblong hole the guide structure has the greatest distance from the upper side of the bone plate.

12. A bone plate according to claim 9, wherein the oblong hole has a second guide structure configured to guide bone screws with threadless head and neck, and wherein the second guide structure has a trend inclined relative to the surface of the plate and a segment of the second guide structure situated nearest the lower side of the bone plate is in the region of the oblong hole in which the thread flights and the support structure are arranged.

13. A system comprising a bone plate according to claim 1 and at least one bone screw, wherein the bone screw has a thread in a first region and a bearing structure fashioned complementary to the support structure of the oblong hole of the bone plate in a second region, wherein the thread is above the bearing structure on a screw head or neck in a direction along the screw's lengthwise axis.

14. The bone plate described in claim 1, wherein said support structure is provided above and below the thread flights in the direction substantially transverse to the plane of the upper side.

15. A bone plate comprising:
a bottom side for resting against a bone;
an upper side opposite the bottom side in a plane; and
a plurality of holes located along a longitudinal axis of the plate for inserting one or more bone screws to be anchored to a bone, wherein at least one hole is a continuous oblong hole with no barriers protruding into the hole, said oblong hole including
a longitudinal axis running in the direction of the longitudinal axis of the plate,
thread flights provided in a partial area of a lateral side of the oblong hole, the lateral side of the oblong hole having a circular angle around a threaded portion of no more than 180 degrees; and
a support structure with smooth walls configured for a positive fit with a correspondingly configured negative structure at a screw head or screw neck of a bone screw is provided above or below the thread flights in the direction substantially transverse to the plane of the upper side;
wherein said thread flights, when seen in a direction substantially transverse to the plane of the upper side, are arranged only over a part of the depth of the oblong hole and extend along a shorter contour segment of the oblong hole than the smooth-wall support structure.

16. The bone plate as described in claim 15, the oblong hole having two arcuate segments at opposite ends and two substantially parallel linear portions connecting the arcuate segments.

17. The bone plate as described in claim 15, wherein the support structure has a circular angle larger than the circular angle of the threaded portion.

18. The bone plate as described in claim 15, wherein the circular angle of the support structure is within the range of 185 to 300 degrees.

19. The bone plate described in claim 15, wherein said support structure is provided above and below the thread flights in the direction substantially transverse to the plane of the upper side.

20. A bone plate comprising:
a bottom side for resting against a bone;
an upper side opposite the bottom side in a plane; and
a plurality of holes located along a longitudinal axis of the plate for inserting one or more bone screws to be anchored to a bone, wherein at least one oblong hole includes first and second arcuate segments at opposite ends of the hole and two substantially parallel linear portions connecting the first and second arcuate segments, the oblong hole including
a longitudinal axis between the two arcuate segments running in the direction of the longitudinal axis of the plate,
thread flights provided in a partial area of a lateral side of the oblong hole proximate the first arcuate segment, a circular angle around which the threaded flights extend is at a maximum of 180 degrees; and
a support structure with smooth walls configured for a positive fit with a correspondingly configured negative structure at a screw head or screw neck of a bone screw is provided above or below the thread flights in the direction substantially transverse to the plane of the upper side and proximate the second arcuate segment;

wherein the thread flights, when seen in a direction substantially transverse to the plane of the upper side, are arranged only over a part of the depth of the oblong hole and extend along a shorter contour segment of the oblong hole than the smooth-wall support structure.

21. The bone plate as described in claim 20, wherein the support structure has a circular angle that is larger than the circular angle of the threaded portion.

22. The bone plate as described in claim 20, wherein the circular angle of the support structure is within the range of 185 to 300 degrees.

23. The bone plate described in claim 20, wherein said support structure is provided above and below the thread flights in the direction substantially transverse to the plane of the upper side.

* * * * *